United States Patent [19]

Yafuso et al.

[11] Patent Number: 4,954,318

[45] Date of Patent: Sep. 4, 1990

[54] OPTICAL SENSOR

[75] Inventors: Masao Yafuso, El Toro; Cheng F. Yan, Irvine; Thomas G. Hacker, Anaheim; Henry K. Hui, Irvine; Thomas P. Maxwell; William W. Miller, both of Santa Ana, all of Calif.

[73] Assignee: Minnesota Mining and Manufacturing Company, St. Paul, Minn.

[21] Appl. No.: 91,432

[22] Filed: Aug. 31, 1987

[51] Int. Cl.[5] ............................................. G01N 21/77
[52] U.S. Cl. ........................................ 422/59; 422/56; 422/57; 422/68; 422/87; 422/82.08; 422/82.09; 436/68; 436/167; 436/172; 128/634; 350/96.29; 356/39; 250/227.11
[58] Field of Search .................... 422/55–58, 422/68, 59, 83, 86, 87; 436/68, 164, 167, 172, 805; 350/96.29; 356/39; 250/227; 128/634

[56] References Cited

U.S. PATENT DOCUMENTS

| | | | |
|---|---|---|---|
| 4,516,580 | 5/1985 | Polanyi | 436/68 X |
| 4,557,900 | 12/1985 | Heitzmann | 422/55 |
| 4,657,736 | 4/1987 | Marsoner et al. | 422/56 |
| 4,737,343 | 4/1988 | Hirschfeld | 436/172 X |
| 4,771,006 | 9/1988 | Miller et al. | 436/164 X |
| 4,803,049 | 2/1989 | Hirschfeld et al. | 422/58 |
| 4,810,658 | 3/1989 | Shanks et al. | 422/68 X |
| 4,824,789 | 4/1989 | Yafuso et al. | 436/68 |
| 4,849,172 | 7/1989 | Yafuso et al. | 436/172 X |

Primary Examiner—Robert J. Warden
Assistant Examiner—Lynn M. Kummert
Attorney, Agent, or Firm—Donald M. Sell; Walter N. Kirn; Dale E. Hulse

[57] ABSTRACT

An apparatus for measuring the concentration of a component in a medium comprising:

an optical sensor including at least one optical indicator for providing an optical signal which varies in response to the presence of a component in a medium;

an optical signal fiber capable of transmitting the optical signal from the optical sensor; and a supply reservoir associated with the optical sensor and acting to provide additional optical indicator to the optical sensor.

25 Claims, 1 Drawing Sheet

U.S. Patent  Sep. 4, 1990  4,954,318
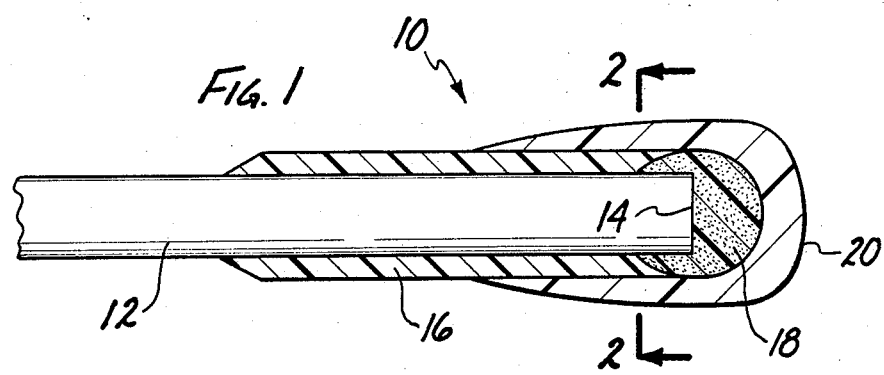
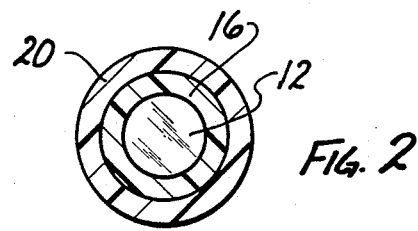
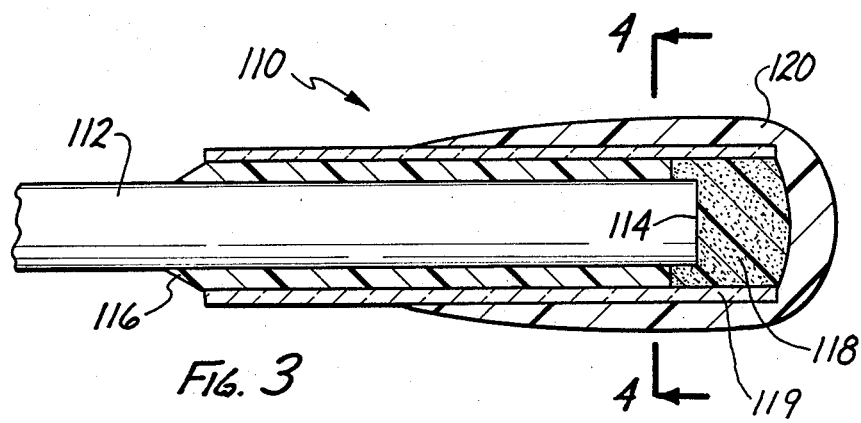
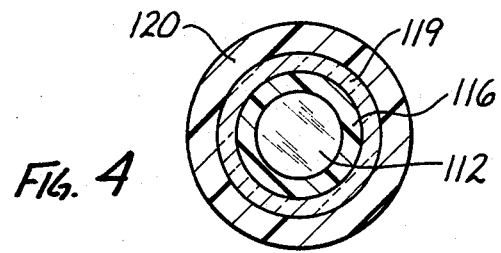

OPTICAL SENSOR

BACKGROUND OF THE INVENTION

The present invention relates to a sensing or measuring apparatus which includes an optical sensor and to a method for using such an apparatus. More particularly, the invention relates to such an apparatus and method which involve an optical indicator in the sensor that is depleted or deteriorates with time or use.

Optical sensors are quite useful in systems to measure the concentration of a component in a medium. For example, optical sensors can be effectively employed for measuring or monitoring a given component in blood. Typical components measured by optical sensors include gases, such as oxygen and carbon dioxide, hydrogen ions (pH), electrolytes, glucose and the like. Certain of such optical sensors are disclosed in commonly assigned U.S. patent application Ser. Nos. 917,912 and 917,913, each of which is incorporated in its entirety by reference herein.

Such optical sensors include an optical indicator, e.g., a fluorescent dye, which interacts with the component to be sensed or measured. Typically, the optical indicator, often in combination with a component permeable matrix, is placed on or directly adjacent to the optical surface of an optical signal means, e.g., an optical fiber. The interaction between the optical indicator and the component to be sensed or measured is monitored utilizing optical signals carried by the optical signal means.

The accuracy of the component concentration measurement or determination made by systems including such optical sensors is dependent, among other factors, upon maintaining a relatively constant amount of active optical indicator in signal communication with the optical signal means. However, during fabrication and use of the optical sensor, at least a portion of the active optical indicator is often destroyed or lost, thus adversely affecting the integrity of the signals transmitted by the optical signal means as being indicative of the true concentration of the component in a medium. This problem is particularly troublesome in situations where it is desired to monitor the concentration of a component over a relatively long period of time.

SUMMARY OF THE INVENTION

A new apparatus and method for measuring the concentration of a component in a medium have been discovered. In one broad aspect, the present system comprises an optical sensor means, an optical signal means and an optical indicator supply means, which acts to provide additional optical indicator to the optical sensor means, preferably on a substantially continuous basis. This apparatus reduces the loss of signal integrity caused by the loss or deterioration of optical indicator in the optical sensor means. This results in more consistent determinations of component concentration over a period of time, and is particularly valuable in monitoring a component, especially oxygen, concentration (partial pressure) in a medical patient's blood, e.g., on a substantially continuous basis, over a relatively protracted period of time.

In another broad aspect, the invention involves a method for measuring the concentration of a component in a medium utilizing an optical sensor and comprises supplying additional optical indicator to the optical sensor. Supplying additional optical indicator preferably acts to at least partially maintain the amount of optical indicator in the optical sensor, thereby preferably improving the consistency of response of the optical sensor to the component being measured.

The presently useful optical indicators preferably function by modifying a light signal, e.g., in an optical fiber, in response to the presence of a certain component, e.g., oxygen, in an aqueous medium, e.g., blood. The preferred optical indicators for use in the present system are selected from the group consisting of fluorescence indicators, absorbance indicators and mixtures thereof, with fluorescence indicators being especially preferred. For example, fluorescence indicators often include a dye which is sensitive or responsive to a component. This dye can be placed on the tip of an optical fiber and exposed to the aqueous medium containing the component of interest. By monitoring the light signals from the dye tipped optical fiber, the concentration (partial pressure) of the component in the aqueous medium can be determined.

As noted above, the present optical signal means acts to transmit an optical signal from the optical sensor. The optical signal to be transmitted is influenced by or in response to the presence of the component of interest in the medium. This optical signal means is preferably further capable of delivering a source signal, e.g., excitation light, to the optical sensor. In one embodiment, the optical signal means comprises an optical fiber for (1) delivering excitation light to the optical sensor so that the optical indicator in the optical sensor can provide an optical signal which is influenced by or is in response to the component of interest; and (2) transmitting this optical signal from the optical sensor.

In addition to the optical indicator, the optical sensor preferably further includes a component permeable, polymeric matrix. By "component permeable" is meant that the substance in question, e.g., the polymeric matrix, is permeable to the component the concentration of which is to be determined using the optical sensor. Any suitable polymeric matrix may be employed. The polymeric matrix should have no substantial adverse effect on the other components of the present system or on the operation of this system and method. One particularly useful class of polymeric matrixes is selected from the group consisting of silicone polymers and mixtures thereof. Such polymers are especially useful if oxygen is the component of interest. Although various forms of silicone can be employed for the matrix, it is important that the silicone have a high permeability to the gas of interest so that the sensitivity of the optical indicator to the gas of interest is optimized. For example, the silicone polymer may be dimethylsiloxane, diphenylsiloxane, or a diphenyldimethylsiloxane copolymer. Of this group, dimethylsiloxane is preferred because of its high gas permeability. It is of course realized that other members of the homologous series which include the before mentioned polymers might also be used.

The polymeric matrix is preferably cross-linked to provide improved support and structure for the optical indicator included in the optical sensor. The term "cross-linking" as used herein refers to a chemical reaction in which polymeric molecules are reacted with multi-functional, e.g., difunctional, compounds to join the polymeric molecules together by bridges or crosslinks derived from the multi-functional compounds or crosslinking agents.

Various cross-linking agents and cross-linking catalysts may be employed to cross-link the polymeric matrix. Such agents and catalysts should have no substantial detrimental effect on the present apparatus or method. The cross-linking reaction may be conducted in a conventional manner and, therefore, is not discussed in detail here.

If oxygen is the component of interest, the optical indicator is preferably selected from the group consisting of polynuclear aromatic compounds, derivatives of polynuclear aromatic compounds and mixtures thereof. More preferably, the optical indicator is a mixture of derivatives of polynuclear aromatic compounds, in particular tertiary butyl derivatives of decacyclene. Certain of these preferred optical indicators are described in commonly assigned U.S. patent application Ser. No. 853,460, filed Apr. 18, 1986, which application is incorporated in its entirety by reference herein.

The presently useful optical indicator supply means or reservoir means is associated with the optical sensor and acts to provide a supply, preferably a substantially continuous supply of additional optical indicator to the optical sensor means. The supply means is preferably situated so that the optical indicator in the supply means has substantially no effect on the optical signal from the optical sensor. In other words, it is preferred that the optical indicator from the supply means becomes "active", i.e., responsive to the component of interest, only after becoming part of the optical sensor. This feature is important because if the optical indicator in the supply means interacts with the component of interest, the optical signal transmitted by the optical signal means can become non-indicative of the true concentration of the component in the medium.

In one embodiment, the optical indicator in the supply means is preferably combined with a matrix material, preferably a polymeric matrix material, which is substantially component impermeable. By "component impermeable" is meant that the substance in question, e.g., the matrix material, is impermeable to the component of interest. This substantially component impermeable matrix material substantially prevents the component of interest from interacting with the optical indicator in the supply means. Any suitable matrix material may be used in combination with the optical indicator in the supply means. This matrix material should have no substantial detrimental effect on the optical indicator or on the present system or method. Also, the matrix material should be such as to allow the optical indicator in the supply means to migrate or diffuse therethrough into the optical sensor means. The specific matrix material chosen depends on the specific application involved. Suitable matrix materials may be derived from at least one resin selected from the group consisting of epoxy resins, acrylic resins and mixtures thereof. For example, if oxygen is the component of interest and a mixture of t-butyl derivatives of decacyclene is employed as the optical indicator, one especially useful matrix material is an acrylate resin curable by ultra-violet light and sold under the trademark of Dymax 20017A by Dymax Engineering Adhesives. One or more epoxy resins curable by ultra-violet light are also particularly useful matrix materials. Other matrix materials may be employed provided that such matrix materials function as described herein.

The optical sensor or optical sensor means preferably is situated so as to abut, i.e., have one surface in common with, the optical indicator supply means. This feature allows for improved transfer of the optical indicator from the supply means to the optical sensor.

The present apparatus preferably further comprises an overcoating at least partially covering, and more preferably acting to protect, the optical sensor means. This overcoating preferably comprises a component permeable material and an effective amount of an opaque agent. The overcoating should be substantially insoluble in the medium. For example, if blood is the medium, the overcoating is preferably water insoluble. One particularly useful component permeable material for use in the overcoating is cross-linked cellulosic material. Such overcoatings are more fully described in commonly assigned U.S. patent application Ser. No. 049,844, filed May 15, 1987. This application is incorporated in its entirety by reference herein.

These and other aspects and advantages of the present invention are set forth in the following detailed description and claims, particularly when considered in conjunction with the accompanying drawing in which like parts bear like reference numerals.

BRIEF DESCRIPTION OF THE DRAWINGS

FIG. 1 is a side view, in cross section, of one embodiment of the present apparatus.

FIG. 2 is a cross-sectional view taken along line 2—2 of FIG. 1.

FIG. 3 is a side view, in cross-section, of another embodiment of the present apparatus.

FIG. 4 is a cross-sectional view taken along line 4—4 of FIG. 3.

DETAILED DESCRIPTION OF THE INVENTION

Referring now to FIGS. 1 and 2, a first sensor, shown generally at 10, includes an optical fiber 12 which has an optical surface 14, a dye supply layer 16, a sensing element 18 and an overcoating 20.

Sensing element 18 is positioned directly up against and adjacent to optical surface 14 and down along the sides of the distal tip of optical fiber 12. Sensing element 18 includes an optical indicator, e.g., a fluorescent dye, dispersed in a polymeric matrix, which is permeable to the component to be sensed by first sensor 10.

Dye supply layer 16 surrounds the sides of optical fiber 12 a distance away from the distal tip of optical fiber 12. As shown in FIG. 1, dye supply layer 16 abuts sensing element 18 so that no void space exists between dye supply layer 16 and sensing element 18. In other words, dye supply layer 16 is in direct contact with sensing element 18. Dye supply layer 16 includes an amount of the same optical indicator as is present in sensing element 18, and a substantially component impermeabe matrix material. The optical indicator in dye supply layer 16 is dispersed in the matrix material, which is preferably a polymeric matrix material. In one modification, the optical indicator in dye supply layer 16 may be a precursor of the optical indicator present in sensing element 18, provided that this precursor is converted to the optical indicator at the conditions present in sensing element 18.

Covering sensing element 18 and a portion of supply layer 16 is overcoating 20. Substantially the entire exposed area of sensing element 18 is covered by overcoating 20. Overcoating 20 includes an opaque agent dispersed within a component permeable matrix. This matrix is insoluble in the medium, e.g., blood, in which first optical sensor 10 is to be used. Because overcoating 20 completely covers the exposed area of sensing element 18, sensing element 18 has an opaque coating completely around its exposed area. This opaque coating optically isolates sensing element 18 from the optical environment outside of overcoating 20.

Another embodiment of the present invention is shown in FIGS. 3 and 4. In these figures, a second optical sensor, shown generally at 110, includes a second optical fiber 112, which has a second optical surface 114, a second dye supply layer 116, a second sensing element 118, a protective, rigid sleeve 119 and a second overcoating 120.

Second optic fiber 112, second sensing element 118 and second overcoating 120 of second optical sensor 110 are, except as indicated below, structured and function in much the same way as optical fiber 12, sensing element 18 and overcoating 20, respectively, of first optical sensor 10.

Second dye supply layer 116 surrounds a portion of second optical fiber 112 away from the distal tip of second optical fiber 112. In general, second dye supply layer 116 has a composition similar to that of dye supply layer 16 of first optical sensor 10. In addition, the matrix material included in second dye supply layer 116 has adhesive properties and provides adhesive between second optic fiber 112 and rigid protective sleeve 119. As can be seen in FIG. 3, second dye supply layer 116 abuts second sensing element 118 away from the distal tip of second optic fiber 112.

Rigid protective sleeve 119 surrounds and extends out from the distal portion of second optic fiber 112, and acts to stabilize or immobilize this portion of second optic fiber 112 and second sensing element 118.

Second sensing element 118 is placed in the space formed by rigid protective sleeve 119, second dye supply layer 116 and second optical surface 114. Second sensing element 118 is placed directly against, in abutting relation to, both second optical surface 114 and second dye supply layer 116.

Second overcoating 120 surrounds and is adhered to the distal end of rigid protective sleeve 119.

Both first optical sensor 10 and second optical sensor 110 function, in general as follows. This functioning is described with respect to first optical sensor 10, it being understood that, unless stated to the contrary, second optical sensor 110 functions in a similar manner. Optical sensor 10 is placed in a medium, e.g., blood, containing the component to be sensed/measured.

Optic fiber 12 is used to provide excitation light to sensing element 18 and to transmit a signal from sensing element 18 which varies in response to the concentration or partial pressure of the component of interest in the medium. This response signal is then interpreted to determine the concentration or partial pressure of the component in the medium. This optical sensor 10 is used to continuously monitor the concentration or partial pressure of the component of interest in the medium. In order to get consistent results, it is desirable to maintain the amount of optical indicator in sensing element 18 exposed to the excitation light at a substantially constant level.

Over a period of time, a portion of the optical indicator in sensing element 18 becomes inactive or otherwise ineffective to interact with the component of interest. The optical indicator from dye supply layer 16 passes into sensing element 18 to at least partially replenish, preferably substantially maintain, the amount of optical indicator in sensing element 18. This replenishing or maintaining of the optical indicator content of sensing element 18 by dye supply layer 16 is accomplished on a substantially continuous basis without taking first optical sensor 10 out of service. This is quite important in the medical applications for this system where accurate and consistent results are necessary, often over a relatively long period of time and without removing the sensor from the patient or otherwise changing the sensor. This replenishing or maintaining feature of the present invention substantially prolongs the useful life of first optical sensor 10 relative to a similar sensor with no dye supply layer 16. More reliable and consistent analytical results, especially over a relatively long period of time, can be achieved.

The following representative, non-limiting examples illustrate certain aspects of the present invention.

EXAMPLE 1

A blood oxygen sensor, similar in construction to first optical sensor 10 is used to monitor the oxygen partial pressure in blood on a substantially continuous basis over a period of time.

In this blood oxygen sensor, sensing element 18 is composed of an oxygen permeable, cross-linked dimethylsiloxane polymeric matrix with the optical indicator being a mixture of t-butyl derivatives of decacyclene. Overcoating 20 is composed of water insoluble, oxygen permeable, cross-linked cellulosic material in which an opaque agent, copper phthalocyanine, is dispersed. Dye supply layer 16 is composed of an acrylate resin which is cured by exposure to ultra violet light and, dispersed therein, an amount of the above-noted mixture of t-butyl derivatives of decacyclene. This acrylate resin is sold under the trademark Dymax 20017A, by Dymax Engineering Adhesives. This entire blood oxygen sensor is sufficiently small to be suitable for use in vivo in the treatment of a medical patient.

After a period of time in use, this blood oxygen sensor continues to provide consistent monitoring of the oxygen partial pressure of the blood.

EXAMPLE 2

A blood oxygen sensor, similar in construction to second optical sensor 110 is used to monitor the oxygen partial pressure in blood on a substantially continuous basis over a period of time.

In this blood oxygen sensor, second sensing element 118, second overcoating 120, and second dye supply layer 116 are composed of similar materials as sensing element 18, dye supply layer 16 and overcoating 20, respectively, in Example 1. Rigid protective sleeve 119 is made of glass. This entire blood oxygen sensor is sufficiently small to be suitable for use in vivo in the treatment of a medical patient.

After a period of time in use, this blood oxygen sensor continues to provide consistent monitoring of the oxygen partial pressure of the blood.

While the present invention has been described with respect to various specific examples and embodiments, it is to be understood that the present invention is not limited thereto and that it can be variously practiced within the scope of the following claims.

What is claimed is:

1. An apparatus for measuring the concentration of a component in a medium comprising:
   optical sensor means including at least one optical indicator, which optical indicator provides an optical signal which varies according to the concentration of a component in a medium;

optical signal receiving means for receiving said optical signal from said optical sensor means; and supply means containing additional optical indicator, said supply means being positioned adjacent to said optical sensor means and acting to provide said additional optical indicator to said optical sensor means.

2. The apparatus of claim 1 wherein said supply means provides said additional optical indicator substantially continuously to said optical sensor means.

3. The apparatus of claim 1 wherein said optical sensor means further comprises a component permeable, polymeric matrix which holds said at least one optical indicator.

4. The apparatus of claim 3 wherein said component permeable, polymeric matrix comprises a silicone polymer.

5. The apparatus of claim 1 wherein said at least one optical indicator is selected from the group consisting of fluorescence indicators and absorbance indicators.

6. The apparatus of claim 1 wherein said at least one optical indicator is a fluorescence indicator.

7. The apparatus of claim 1 wherein said optical signal receiving means further comprises means for delivering excitation light to said optical sensor means.

8. The apparatus of claim 7 wherein said optical signal receiving means comprises an optical fiber.

9. The apparatus of claim 1 wherein said supply means is positioned so that said additional optical indicator in said supply means has substantially no effect on said optical signal from said optical sensor means.

10. The apparatus of claim 1 wherein said additional optical indicator in said supply means is combined with a matrix material which is substantially component impermeable.

11. The apparatus of claim 10 wherein said substantially component impermeable matrix material is polymeric.

12. The apparatus of claim 11 wherein said polymeric matrix material is derived from at least one resin selected from the group consisting of epoxy resins, acrylic resins and mixtures thereof.

13. The apparatus of claim 1 wherein said optical sensor means abuts said supply means.

14. The apparatus of claim 1 wherein said at least one optical indicator comprises an optical indicator which senses oxygen.

15. The apparatus of claim 1 wherein said at least one optical indicator comprises an optical indicator which senses carbon dioxide.

16. The apparatus of claim 1 wherein said at least one optical indicator comprises an optical indicator which senses hydrogen ions.

17. The apparatus of claim 1 wherein said at least one optical indicator comprises an optical indicator which senses glucose.

18. The apparatus of claim 1 wherein said at least one optical indicator comprises an optical indicator which sense an electrolyte.

19. The apparatus of claim 1 wherein said at least one optical indicator comprises an optical indicator which provides an optical signal which varies according to the concentration of a component in blood.

20. The apparatus of claim 19 wherein said at least one optical indicator comprises an optical indicator which senses oxygen.

21. The apparatus of claim 19 wherein said at least one optical indicator comprises an optical indicator which senses carbon dioxide.

22. The apparatus of claim 19 wherein said at least one optical indicator comprises an optical indicator which senses hydrogen ions.

23. The apparatus of claim 1 wherein said additional optical indicator in said supply means is stored in a solid polymeric matrix which releases said additional optical indicator over time so as to keep the level of optical indicator in said optical sensor means at a relatively constant level.

24. In an apparatus for measuring the concentration of a component in a medium which apparatus includes an optical sensor having at least one optical indicator therein for providing an optical signal which varies according to the concentration of the component in the medium and optical signal receiving means for receiving said optical signal from said optical sensor, wherein the improvement comprises: supply means containing additional optical indicator, said supply means being positioned adjacent to said optical sensor so as to provide said additional optical indicator to said optical sensor.

25. The apparatus of claim 24 wherein said supply means comprises means for providing said additional optical indicator substantially continuously to said optical sensor.

* * * * *

UNITED STATES PATENT AND TRADEMARK OFFICE
CERTIFICATE OF CORRECTION

PATENT NO. : 4,954,318

DATED : September 4, 1990

INVENTOR(S) : Masao Yafuso et al.

It is certified that error appears in the above-identified patent and that said Letters Patent is hereby corrected as shown below:

Column 8, line 12, "sense" should be --senses--.

Signed and Sealed this

Thirty-first Day of December, 1991

Attest:

HARRY F. MANBECK, JR.

*Attesting Officer*  *Commissioner of Patents and Trademarks*